(12) United States Patent
Dominick et al.

(10) Patent No.: US 10,521,554 B2
(45) Date of Patent: Dec. 31, 2019

(54) HARMONIZATION OF CROSS-VENDOR DATA

(71) Applicant: Siemens Healthcare GmbH, Erlangen (DE)

(72) Inventors: Lutz Dominick, Eggolsheim (DE); Vladyslav Ukis, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 931 days.

(21) Appl. No.: 14/885,453

(22) Filed: Oct. 16, 2015

(65) Prior Publication Data

US 2017/0109472 A1 Apr. 20, 2017

(51) Int. Cl.
*G06F 19/00* (2018.01)
(52) U.S. Cl.
CPC .................................. *G06F 19/321* (2013.01)
(58) Field of Classification Search
None
See application file for complete search history.

(56) References Cited

U.S. PATENT DOCUMENTS

| | | | | |
|---|---|---|---|---|
| 6,456,239 | B1* | 9/2002 | Werb | G01S 5/02 235/385 |
| 2005/0192838 | A1* | 9/2005 | Jones | G06F 19/324 705/2 |
| 2012/0143625 | A1* | 6/2012 | Eaves | G06F 19/321 705/3 |
| 2015/0320365 | A1* | 11/2015 | Schulze | G06F 3/0484 600/408 |

\* cited by examiner

*Primary Examiner* — Valerie Lubin
(74) *Attorney, Agent, or Firm* — Harness, Dickey and Pierce, P.L.C.

(57) ABSTRACT

A data harmonization system including a data harmonization server; and one or more client devices configured to communicate with the data harmonization server. The one or more client devices may have a processor configured to transform, using a template, medical data having a first format to transformed medical data having a second format, determine whether the transformed medical data is harmonized medical data or un-harmonized medical data based on the transformed medical data and a medical imaging standard, and send the transformed medical data to a data harmonization server, if the processor determines that the medical data is un-harmonized medical data. The medical data may have a vendor specific dialect of the medical imaging standard and the harmonized medical data may have a generic version of the medical imaging standard.

18 Claims, 6 Drawing Sheets

HARMONIZATION OF CROSS-VENDOR DATA

BACKGROUND

Field

One or more example embodiments relate to a system, device and/or method to facilitate compatibility between applications and data utilized therewith.

Description of Related Art

Applications, for example medical applications, may run in heterogeneous environments that utilize non-uniform vendor specific semantic data structures. These data structures may contain, for example, medical images, patient data, scanner protocols, medical data for business intelligence reports and dose management, etc.

Standards and regulations such as Digital Imaging and Communications in Medicine (DICOM) and Integrating the Healthcare Enterprise (IHE), attempt to standardize communication and data structures in the medical field. However, various factors (e.g., business needs, application features, and scanner protocols) may require changes to the applications before the aforementioned standards are updated, thus, leading to vendor specific dialects of a standard. Further, legacy scanners, picture archiving and communication system (PACS), and other data sources may have a relatively long lifecycle that results in some devices running according to antiquated versions of the aforementioned standards, which, in turn, may increase the variability in data structures. Therefore, conventionally, it may be difficult to add new features while ensuring that the system can continue to process existing data.

SUMMARY

This section provides a general summary of the disclosure, and is not a comprehensive disclosure of its full scope or all of its features.

At least some example embodiments relate to a medical server.

In some example embodiments, the medical server includes a processor; and a memory configured to store computer readable code therein that, when executed by the processor, configures the processor to, transform, using a template, medical data having a first format to transformed medical data having a second format, determine whether the transformed medical data is harmonized medical data or un-harmonized medical data based on the transformed medical data and a medical imaging standard, and send the transformed medical data to a data harmonization server, if the processor determines that the medical data is un-harmonized medical data.

In some example embodiments, the processor is configured to provide the harmonized medical data medical data to an application, if the processor determines that the transformed medical data is the harmonized medical data.

In some example embodiments, the processor is configured to provide the harmonized medical data to a front-end of the application, if the processor determines that the transformed medical data is the harmonized medical data.

In some example embodiments, the processor is configured to identify the template from among a plurality of templates stored in the memory based on information within a header of the medical data.

In some example embodiments, the processor is configured to transmit an error message to the data harmonization server, if the processor is unable to identify the template from among the plurality of templates.

In some example embodiments, the processor is configured to anonymize the un-harmonized medical data prior to sending the un-harmonized medical data to the data harmonization server.

In some example embodiments, the medical server further includes an interface configured to communicate with the data harmonization server, and the processor is configured to receive, via the interface, a new template from the data harmonization server in response to sending the un-harmonized medical data thereto.

In some example embodiments, the template is a Data Variability Template (DVT) containing transformation rules for transforming the medical data based on the medical imaging standard.

In some example embodiments, the medical data has a vendor specific dialect of the medical imaging standard and the harmonized medical data is a generic version of the medical imaging standard.

Some example embodiments relate to a data harmonization server.

In some example embodiments, the data harmonization server includes a processor; and a memory configured to store computer readable code therein that, when executed by the processor, configures the processor to, receive un-harmonized medical data from one or more medical servers, and transmit a new template to the one or more medical servers such that the medical servers may generate harmonized medical data therewith based on a medical imaging standard.

In some example embodiments, the processor is configured to receive metadata from the one or more medical servers, the metadata indicating whether a non-functioning template is associated with the un-harmonized medical data.

In some example embodiments, the processor is configured to identify the non-functioning template from among a plurality of templates stored in the memory based on one or more of information within a header of the un-harmonized medical data and the metadata.

In some example embodiments, the processor is configured to recreate an error produced by the one or more medical servers using the non-functioning template, and determine if the new template is compatible with a plurality of medical applications using an associated virtual machine.

In some example embodiments, the data harmonization server is a repository of templates, and the processor is configured to push the new template to all of the one or more medical servers.

In some example embodiments, the processor is configured to periodically push the new template to all of the one or more medical servers.

In some example embodiments, the new template is a Data Variability Template (DVT) containing transformation rules for transforming the un-harmonized medical data based on the medical imaging standard.

In some example embodiments, the un-harmonized medical data received by the data harmonization server is anonymized such that the data harmonization server cannot deduce user information therefrom.

Some example embodiments relate to a data harmonization system.

In some example embodiments, the data harmonization system includes a data harmonization server; and one or more client devices configured to communicate with the data harmonization server.

In some example embodiments, the one or more client devices include a processor configured to, transform, using a template, medical data having a first format to transformed medical data having a second format, determine whether the transformed medical data is harmonized medical data or un-harmonized medical data based on the transformed medical data and a medical imaging standard, and send the transformed medical data to a data harmonization server, if the processor determines that the medical data is un-harmonized medical data.

In some example embodiments, the template is a Data Variability Template (DVT) containing transformation rules for transforming the medical data based on the medical imaging standard.

In some example embodiments, the medical data has a vendor specific dialect of the medical imaging standard and the harmonized medical data is a generic version of the medical imaging standard.

Further areas of applicability will become apparent from the description provided herein. The description and specific examples in this summary are intended for purposes of illustration only and are not intended to limit the scope of the present disclosure.

BRIEF DESCRIPTION OF THE FIGURES

Example embodiments will be described in more detail with regard to the figures, wherein like reference numerals refer to like parts throughout the various figures unless otherwise specified, and wherein.

Figure 1:
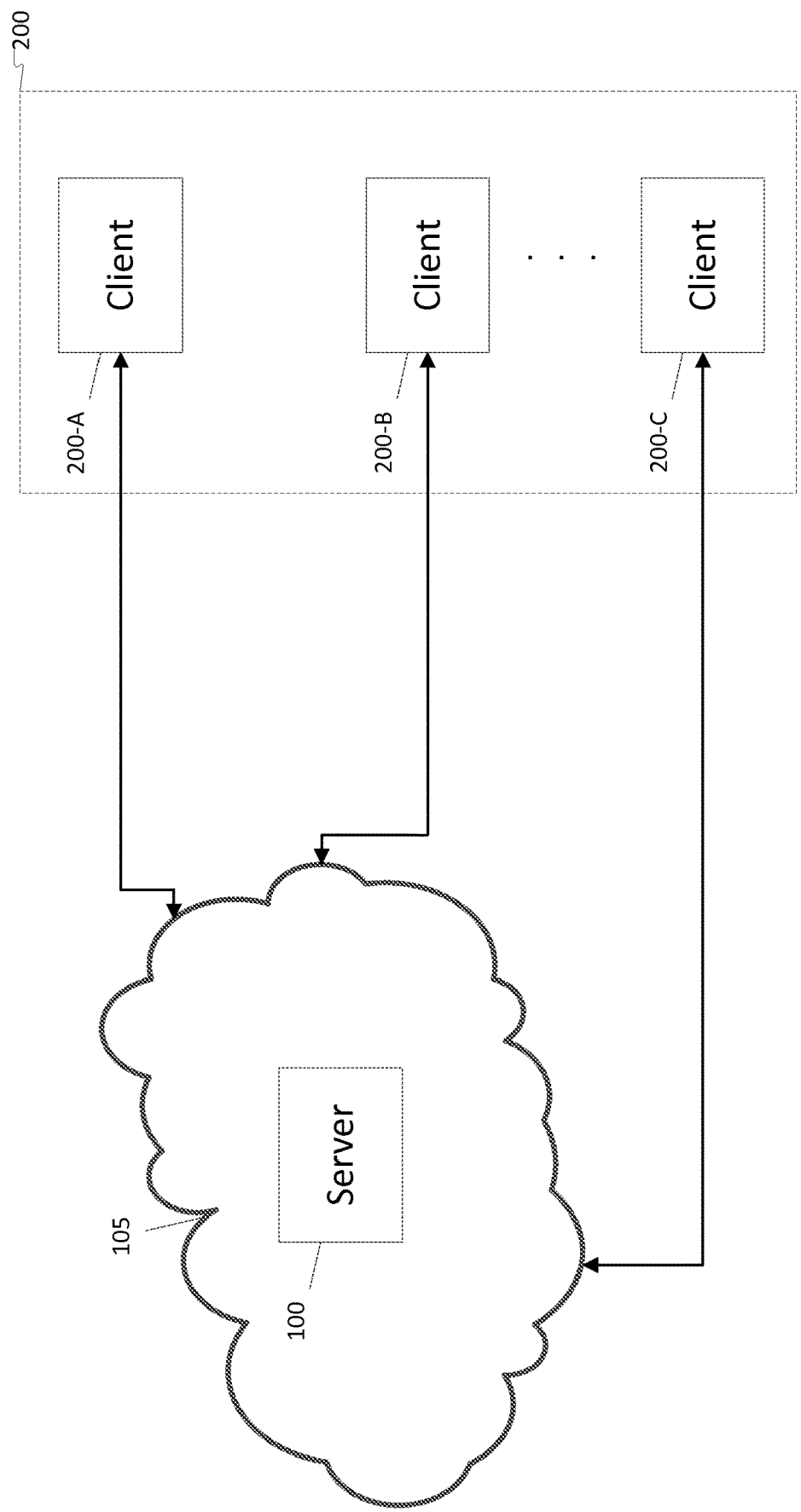
FIG. 1 illustrates a system according to some example embodiments.

It should be noted that these figures are intended to illustrate the general characteristics of methods and/or structure utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments.

DETAILED DESCRIPTION

One or more example embodiments will be described in detail with reference to the accompanying drawings. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated.

Although the terms "first," "second," "third," etc., may be used herein to describe various elements, components, regions, layers, and/or sections, these elements, components, regions, layers, and/or sections, should not be limited by these terms. These terms are only used to distinguish one element, component, region, layer, or section, from another region, layer, or section. Thus, a first element, component, region, layer, or section, discussed below may be termed a second element, component, region, layer, or section, without departing from the scope of this disclosure.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

As used herein, the singular forms "a," "an," and "the," are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups, thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there is no intervening element present.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

FIG. 1 illustrates a system according to example embodiments.

Referring to FIG. 1, a system may include a data harmonization server 100 and client devices 200.

As illustrated in FIG. 1, in some example embodiments the data harmonization server 100 may be within a cloud 105. However, example embodiments are not limited thereto.

The cloud 105 may represent a computing paradigm having a shared pool of converged infrastructure that provides client devices 200 with various capabilities to store and process their data in a third-party data center. The server 100 within the cloud 105 may represent one or more physical servers or virtual machines (VM) that may be dynamically reallocated per demand.

While FIG. 1 illustrates the cloud 105 as containing a data harmonization server 100, the cloud 105 may include other additional elements for proper operation and/or utilization of the cloud 105.

Further, there may be a plurality of client devices 200 connected the server 100 and/or the cloud 105. For example, client devices 200-A to 200-C. The client devices 200 may be medical servers installed at medical facilities, and may include a back-end that processes data and a front-end that provides an interface to users of the client devices 200.

Figure 2:
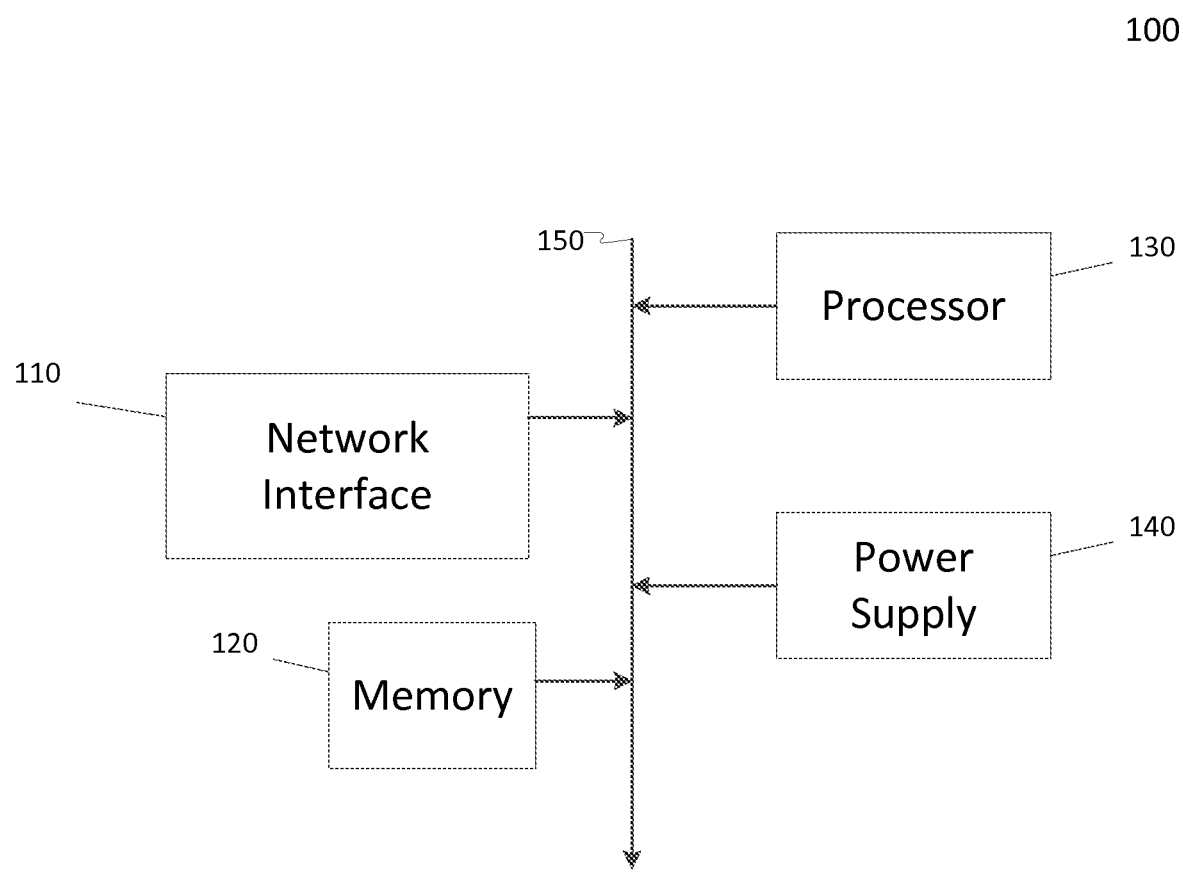
FIG. 2 illustrates a data harmonization server associated with a system according to some example embodiments.

FIG. 2 illustrates a data harmonization server according to example embodiments.

Referring to FIG. 2, the data harmonization server 100 may include, for example, a network interface 110, a memory 120, a processor 130, a power supply 140 and a data bus 150.

One or more of the network interface 110, memory 120, and processor 130 may be adapted to send data to and/or receive data from one another using the data bus 150. Further, the network interface 110, memory 120, and processor 130 may receive operating power from the power supply 140.

The network interface 110 may include a port to receive and/or transmit signals using a transmitter and/or a receiver. The transmitter may include hardware and any necessary software for transmitting signals including, for example, data signals, and control signals, in the network environment. The receivers may include hardware and any necessary software for receiving signals including, for example, data signals and control signals.

The memory 120 may include any device capable of storing data including magnetic storage, flash storage, etc. The memory 120 may store various information utilized by the server 100, for example, Data Variability Templates (DVTs) that are distributed to the client devices 200, as discussed in more detail below.

The processor 130 may include any device capable of processing data including, for example, a microprocessor configured to carry out specific operations based on input data, or capable of executing instructions included in computer readable code. The computer readable code may be stored on, for example, the memory 120.

The processor 130 may include virtual machines such that the memory 120 and the processor 130 include a system pool of vendors that are logically divided into a plurality of different vendor specific systems to replicate each of the plurality of different vendor systems.

Figure 3:
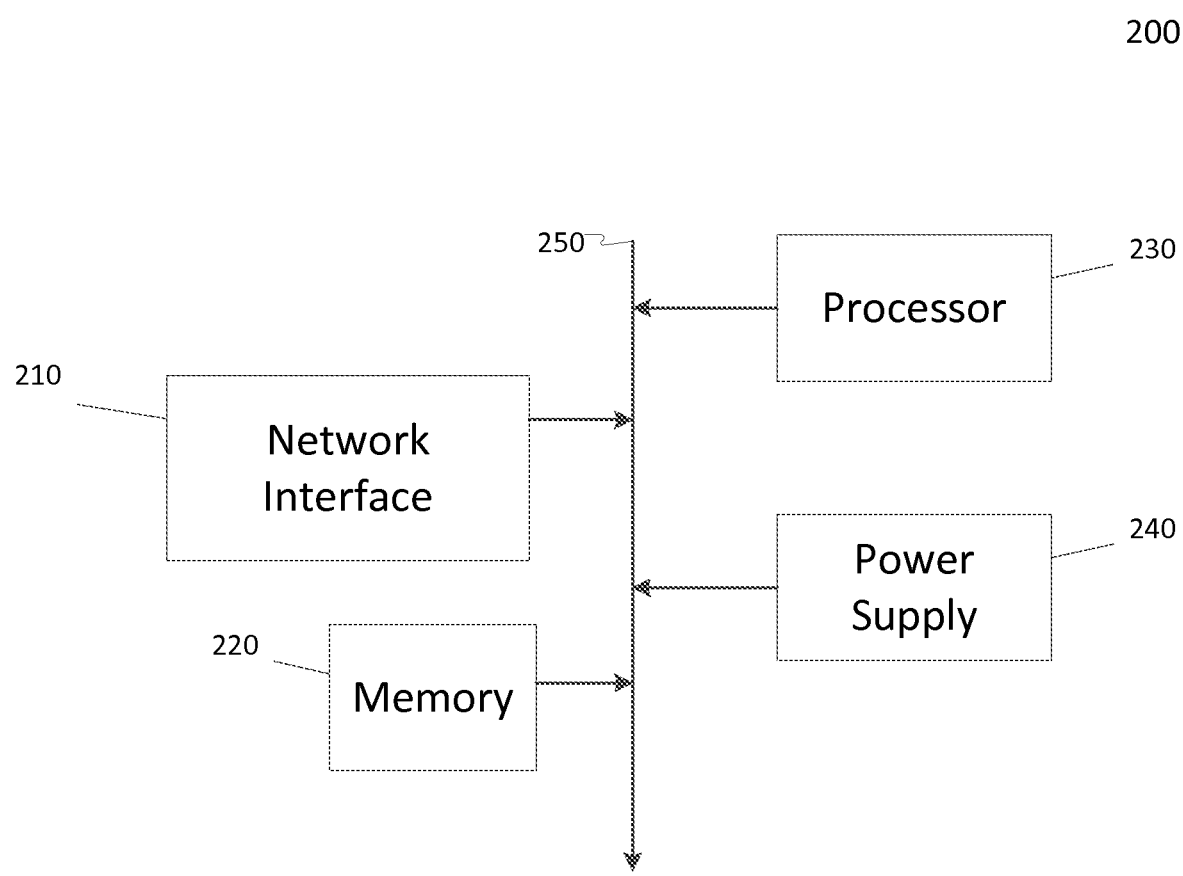
FIG. 3 illustrates a client device associated with a system according to some example embodiments.

FIG. 3 illustrates client devices according to example embodiments.

Referring to FIG. 3, each of the client devices 200 may include, for example, a network interface 210, a memory 220, a processor 230, a power supply 240 and a data bus 250.

One or more of the network interface 210, memory 220, and processor 230 may be adapted to send data to and/or receive data from one another using the data bus 250. Further, the network interface 210, memory 220, and processor 230 may receive operating power from the power supply 240.

The network interface 210 may include a port to receive and/or transmit signals using a transmitter and/or a receiver. The transmitter may include hardware and any necessary software for transmitting signals including, for example, data signals, and control signals, in the network environment. The receivers may include hardware and any necessary software for receiving signals including, for example, data signals and control signals.

The memory 220 may include any device capable of storing data including magnetic storage, flash storage, etc. The memory 120 may store various information utilized by the client devices 200, for example, Data Variability Templates (DVTs) that have been distributed to the client devices 200, as discussed in more detail below.

The processor 230 may include any device capable of processing data including, for example, a microprocessor configured to carry out specific operations based on input data, or capable of executing instructions included in computer readable code. The computer readable code may be stored on, for example, the memory 220.

In some example embodiments, the client devices 200 may be logically and/or physically partitioned into a back-end device and a front-end device (not illustrated). In such embodiments, each of the back-end device and front-end device may include their own respective network interface 210, memory 220, processor 230, power supply 240 and data bus 250.

Figure 4:
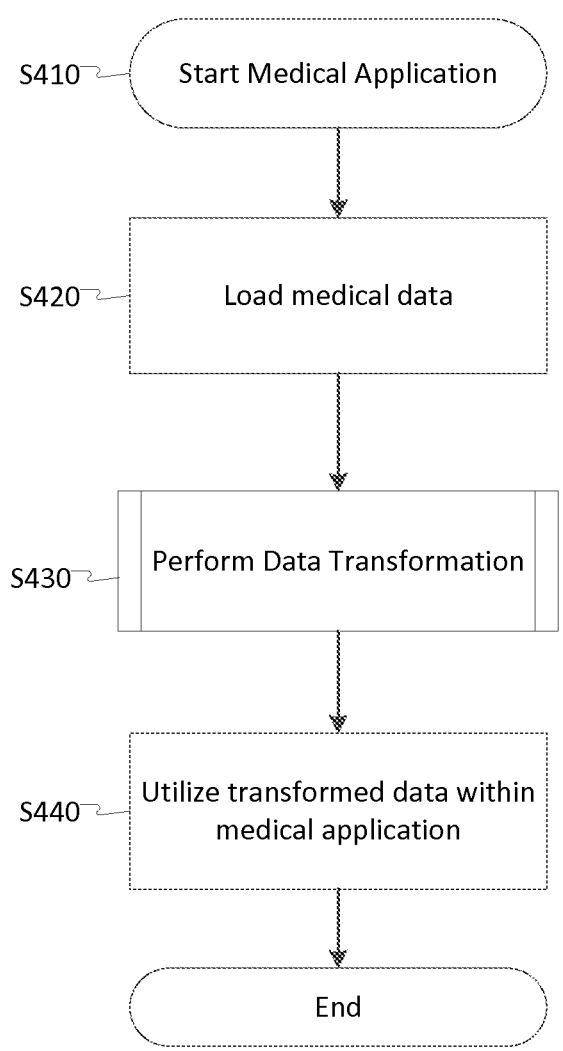
FIG. 4 is a method of utilizing a template to analyze medical data according to some example embodiments.

FIG. 4 is a method of utilizing a template to analyze medical data according to some example embodiments.

Referring to FIG. 4, in operation S410, a user (e.g., a medical professional) may execute a medical application on the client device 200. In some example embodiments, the client device 200 be divided between a front-end client device having a user interface (UI) running thereon and a back end server device.

In operation S420, the client device 200 may temporarily load un-harmonized medical data from a database stored in the memory 220.

The user may be a healthcare practitioner who desires to access patient information or other information at various points in a healthcare workflow. Alternatively, medical personnel may enter new information, such as history, diagnostic, or treatment information, into a medical information system during an ongoing medical procedure.

The medical data may generated by one or more modalities, such as an x-ray system, computed tomography (CT) system, magnetic resonance (MR) system, ultrasound system, digital radiography (DR) system, digital X-ray (DX) system, positron emission tomography (PET) system, single photon emission computed tomography (SPECT) system, nuclear imaging system, and/or other modality.

In some example embodiments, the medical data may include patient medical histories, imaging data, test results, diagnosis information, management information, and/or scheduling information, for example.

The generated medical data may be stored in clinical information systems, such as, hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR).

Many vendors in the medical imaging industry have established a communication standard to allow medical image data to be transmitted and processed by a plurality of disparate systems. One common standard is the Digital Imaging and Communications in Medicine (DICOM) protocol. DICOM is a standard for image and information transmission. DICOM relates to the transfer of electronic data, such as medical images and associated data, between medical diagnostic and imaging systems. The DICOM protocol may be employed in communication between medical devices and image archives, such as Picture Archiving and Communications Systems (PACS).

DICOM standards may outline the data format, flow, and hierarchy of electronic information of diagnostic images and related information between computer systems over TCP/IP networks. For example, the DICOM standard may indicate rules to encode image data from different modalities and accompany the image data with additional medical information that are integrative, for example, information from ECG, pressure curves, to type of equipment employed, etc.

A single DICOM file may include a preamble, a header and image data, for example. The header may identify a data format standard of the DICOM file.

In operation S430, the client device 200 may perform a data transformation on the un-harmonized data using a Data Variability Template (DVT).

For example, often, while the data may contain a header indicating a data format standard the data may not be fully standardized, and instead, utilize vendor specific dialects of a standard and/or an antiquated version of a standard. Therefore, conventionally, the data may not be loaded correctly due to the data being un-harmonized with a medical application.

In contrast, in one or more example embodiments, the client device 200 may transform the data from a dialect to a generic version of the standard to assist the client device 200 with correctly loading the data. For example, in some example embodiments, the client device 200 may perform the operations discussed below with reference to FIG. 5 to determine whether a template and associated medical data are harmonized.

In operation S440, the user may utilize the transformed medical data for example, via an application on the front end of the client device 200.

Figure 5:
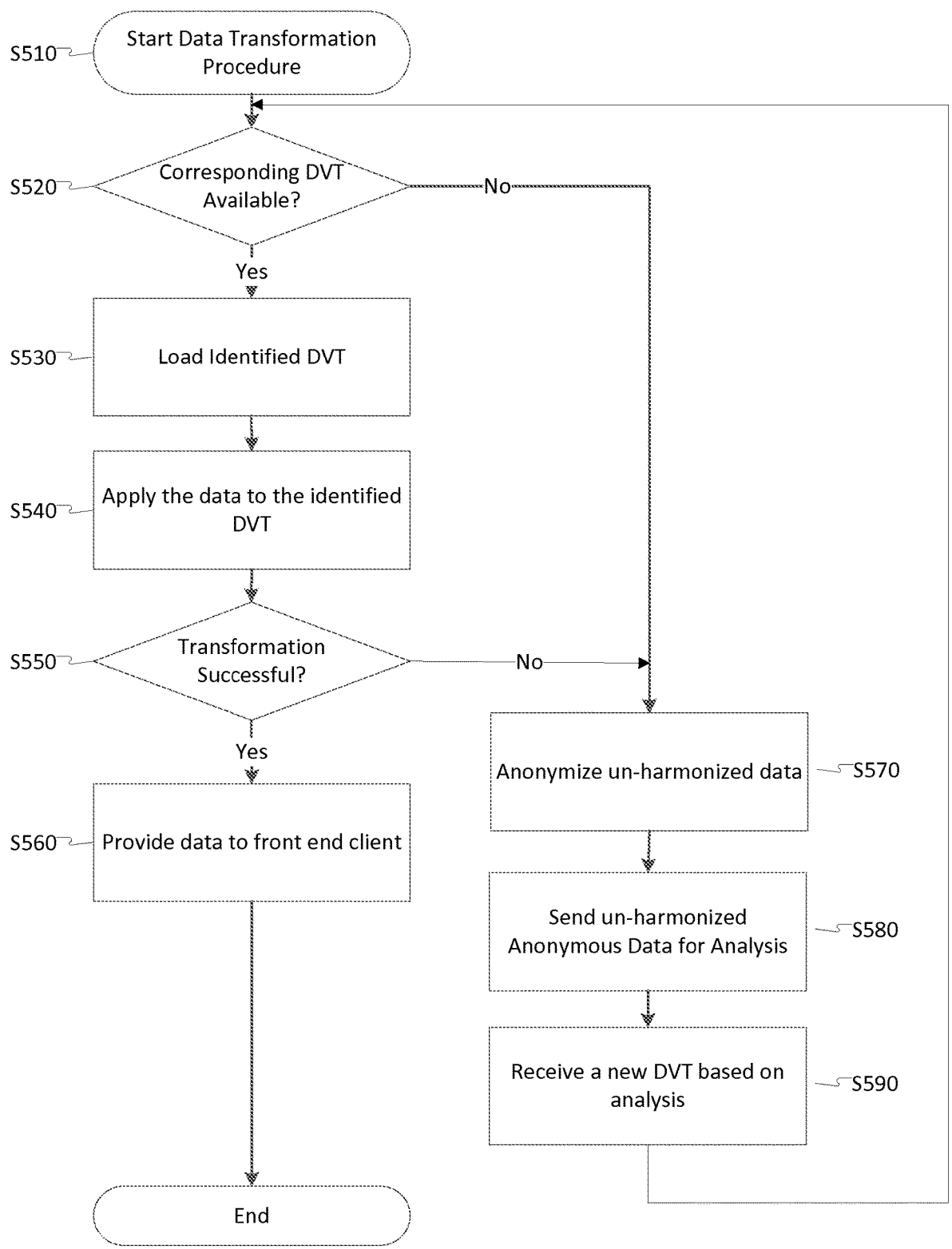
FIG. 5 is a method of determining whether a template and associated medical data are harmonized according to example embodiments.

FIG. 5 is a method of determining whether a template and associated medical data are harmonized according to example embodiments.

In operation S510, the client device 200 may start the data transformation procedure.

In operation S520, the client device 200 may determine whether a corresponding Data Variability Template (DVT) associated with the data is available.

For example, in some example embodiments, the client device 200 may determine whether a template associated with the dialect of the data is stored in the memory 220. For example, the client device 200 may analyze information contained in a header of the data, and select a corresponding DVT based on the information in the header. The template may be identified based by matching the header information with a template based on one or more of the manufacturer or vendor, modality associated with the data (i.e., Computer Tomography), etc. For example, the client device 200 may search for a DVT in the memory 220 indicated as being associated with one or more of the manufacturer, vendor and modality of the data.

In some example embodiments, the templates may be formally described transformation rules that specify the structure and content of a document (or a portion thereof). The templates may impose constraints on the structure and/or content. For example, the templates may specify transformation routes, and relationships between tags contained in the data. For example, the templates may specify rules to transform data from a format associated with the dialect to a format associated with a generic version of the standard.

In some example embodiments, the templates may be Data Variability Templates (DVTs) whose key-value pairs are adjustable. The DVT may be a configurable and extensible JavaScript Object Notation (JSON) schema and data transformation. In some example embodiments, the templates may specify the technical and semantic bi-directional data contract for the vendor specific input data such that the data may be transformed bi-directionally between vendor specific dialects to a generic version of the standard.

In operation S530, the client device 200 may load the identified template. For example, the processor 230 may load the DVT from the memory 220.

In operation S540, the client device 200 may apply the data to the identified DVT to transform the data into standardized data. In some example embodiments, the client device 200 may apply the data to the identified DVT on the back end of the client device 200 without further user interaction. The client device 200 may apply the data to the DVT by mapping the data into application internal object models and data structures identified by the DVT.

In operation S550, the client device 200 may determine whether the data transformation was successful. In some example embodiments, the client device 200 may determine whether a data runtime exception occurred which caused the medical application to crash when loading the data into the DVT. Further, the client device 200 may determine, whether the loaded data generated any error messages, such as an error indicating "undefined data type" was loaded to a cell within the template.

Further still, in other example embodiments, the client device 200 may export the transformed data by performing the by-directional transformation in an attempt to reproduce the original data, and determine if there are any variations between the originally input data sent to the application and the output data from the application. The exported data may be dependent on the internal capabilities (e.g. image viewing and image manipulation) of the application, and, therefore if these capabilities are inconsistent with the DVT, the exported data may not match the input data.

In operation S560, if the client device 200 determines in operation S550 that the data was successfully transformed by the DVT, the client device 200 may provide the transformed data to the front-end of the client device 200, such that the user may analyze the transformed medical data.

In operation S570, if the client device 200 determines in operation S550 that the DVT failed to correctly transform the data, then the data is considered un-harmonized. If the data is un-harmonized, then the client device 200 anonymizes the data by replacing patient specific information therein with anonymous data. In some example embodiments, the client device 200 may replace patient specific fields (e.g., the patients name or other identifying information) with random and/or set (or, alternatively, predefined) anonymous data.

In operation S580, the client device 200 may send the un-harmonized anonymous data to the data harmonization server 100 for analysis. In some example embodiments, the client device 200 may also transmit metadata having information indicating, for example, which DVT the client device 200 utilized when the error occurred, and/or an error message generated at the time of the error.

In operation S590, based on the results of the analysis, the client device 200 may receive a new DVT from the data harmonization server 100. The client device 200 may perform operation S510 to S590 using this new DVT.

Figure 6:
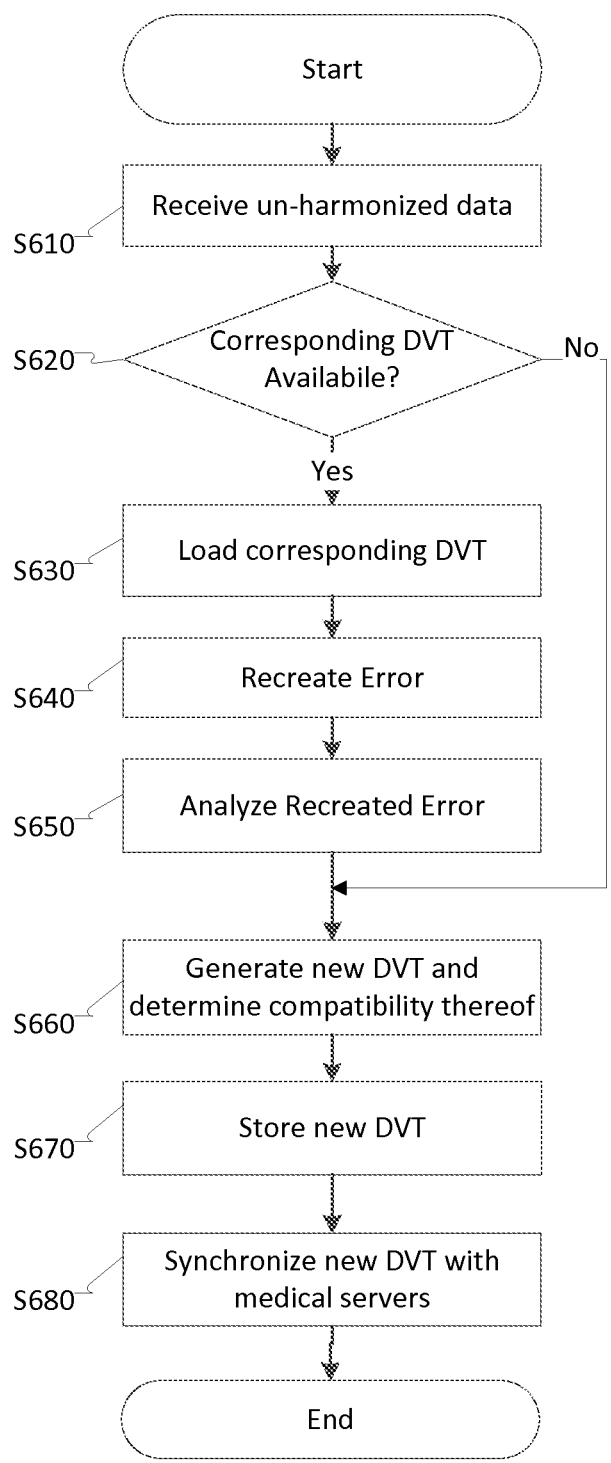
FIG. 6 illustrates a method of operating a data harmonization server according to example embodiments.

FIG. 6 illustrates a method of operating a data harmonization server according to example embodiments.

Referring to FIG. 6, in operation S610, the data harmonization server 100 may receive un-harmonized data from the client device 200. In some example embodiments, the data harmonization server 100 may also receive metadata associated with the un-harmonized data.

In operation S620, the data harmonization server 100 may determine whether a corresponding Data Variability Template (DVT) associated with the data is available.

For example, in some example embodiments, the data harmonization server 100 may analyze the received metadata to determine whether the error code indicates that the client device 200 was unable to find a DVT corresponding to the data. In other example embodiments, the data harmonization server 100 may make a separate determination of whether a DVT is available by, for example, searching a data variability template (DVT) database stored in the memory 120 to determine whether a template is stored therein that is associated with the dialect of the un-harmonized data, for example, by analyzing information contained in a header of the un-harmonized data.

The DVT database may be a centralized store of DVTs that are periodically synchronized with the client devices 200 such that the data harmonization server 100 is a central repository of templates where changes to a single version of the DVT may be replicated to all of the client devices 200.

If, in operation S620, the data harmonization server 100 determines that there is no corresponding DVT, then the data harmonization server 100 may proceed to operation S660, discussed below, to generate a new DVT.

If, in operation S620, the data harmonization server 100 determines that there is a corresponding DVT that incorrectly transformed the data, then in operation S630, the data harmonization server 100 may load the corresponding data variability template (DVT) from the data variability template (DVT) database stored in, for example, the memory 120.

In operation S640, the data harmonization server 100 may attempt to recreate the error. For example, the data harmonization server 100 may apply the un-harmonized data to the identified DVT to recreate the error.

In operation S650, the recreated error may be analyzed. For example, a technician may manually analyze the error and create a new DVT based on the results of the analysis.

For example, a technician may know the error from the metadata transmitted from the client device, the un-harmonized data that was attempted to be translated, and the DVT the caused the error. Therefore, using the knowledge of the DICOM standard, the technician would know the desired value type for the field, and would analyze the un-harmonized input data and the error generated by the DVT to determine how to modify the DVT to correct the error.

In operation S660, the data harmonization server 100 may generate a new DVT based on the analysis and determine the compatibility of new DVT.

For example, data harmonization server 100 may have a system pool of vendor applications available on one or more virtual servers within the data harmonization server 100, and the technician may attempt to transform the data using the new DVT and apply the new data to various ones of the vendor applications running on the virtual servers to assure that the new DVT is compatible with the various vendor applications.

In operation S670, the data harmonization server 100 may store the new DVT. For example, the data harmonization server 100 may store the new DVT in the DVT database stored in the memory 120.

In operation S680, the data harmonization server 100 may synchronize the DVT database with the client devices 200. For example, the data harmonization server 100 may be configured to periodically (e.g., once every 24 hrs) perform a synchronization procedure with each of the client devices 200 to push the new DVTs to the client devices 200. In some example embodiments, the data harmonization server 100 may maintain a list of subscribed client devices 200, and, push the new DVTs to the client devices 200 with a valid subscription via the synchronization procedure.

Therefore, users of the medical system 200 may experience a wide range of data capability due to the receipt of updated DVTs, which may be updated faster than the corresponding standards utilized by vendors, and, thus may lead to fewer errors when loading vendor specific data.

The foregoing description has been provided for purposes of illustration and description. It is not intended to be exhaustive or to limit the disclosure. Individual elements or features of a particular example embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A medical server comprising:
 a processor; and
 a memory configured to store computer readable code therein that, when executed by the processor, configures the processor to,
  receive, a template from a data harmonization server, the template including transformation rules for transforming medical data based on a medical imaging standard, the medical data including at least one of patient medical histories, imaging data and test results, and the transformation rules indicating relationships between tags contained in the medical data to transform the medical data from a first format to a second format, each of the first format and the second format being associated with a same modality,
  transform, using the transformation rules in the template, the medical data having the first format to transformed medical data having the second format,
  determine whether the transformed medical data is harmonized medical data or un-harmonized medical data by comparing the transformed medical data with the medical imaging standard such that the processor determines that the transformed medical data is the un-harmonized medical data in response to the transformed medical data being noncompliant with the medical imaging standard, and send, via an interface, the transformed medical data to the data harmonization server, in response to the processor determining that the medical data is un-harmonized medical data.

2. The medical server of claim 1, wherein the computer readable code, when executed, configures the processor to provide the harmonized medical data medical data to an application, in response to the processor determining that the transformed medical data is the harmonized medical data.

3. The medical server of claim 2, wherein the computer readable code, when executed, configures the processor to provide the harmonized medical data to a front-end of the application, in response to the processor determining that the transformed medical data is the harmonized medical data.

4. The medical server of claim 1, wherein the computer readable code, when executed, configures the processor to identify the template from among a plurality of templates stored in the memory based on information within a header of the medical data.

5. The medical server of claim 4, wherein the computer readable code, when executed, configures the processor to transmit an error message to the data harmonization server, in response to the processor determining that the processor is unable to identify the template from among the plurality of templates.

6. The medical server of claim 1, wherein the computer readable code, when executed, configures the processor to anonymize the un-harmonized medical data prior to sending the un-harmonized medical data to the data harmonization server.

7. The medical server of claim 6, further comprising:
the interface configured to communicate with the data harmonization server, wherein
the computer readable code, when executed, configures the processor to receive, via the interface, a new template from the data harmonization server in response to sending the un-harmonized medical data thereto.

8. The medical server of claim 1, wherein
the template is a Data Variability Template (DVT) containing the transformation rules for transforming the medical data based on the medical imaging standard, the transformation rules indicating relationships between tags contained in the medical data to transform the medical data from the first format associated with a vendor specific dialect of the medical imaging standard to the second format associated with a generic version of the medical imaging standard, and
the processor is configured to transform the medical data having the first format to the transformed medical data having the second format based on the relationships between the tags indicated by the transformation rules.

9. A data harmonization server comprising:
a processor; and
a memory configured to store computer readable code therein that, when executed by the processor, configures the processor to,
generate and transmit a template to one or more medical servers, the template including transformation rules for transforming medical data based on a medical imaging standard, the medical data including at least one of patient medical histories, imaging data and test results, and the transformation rules indicating relationships between tags contained in the medical data to transform the medical data from a first format to a second format, each of the first format and the second format being associated with a same modality,
receive, via an interface, un-harmonized medical data from the one or more medical servers and metadata, the metadata indicating the template that generated the un-harmonized medical data is a non-functioning template,
generate a new template based on the un-harmonized medical data and the non-functioning template, and
transmit, via the interface, the new template to the one or more medical servers such that the medical servers may generate harmonized medical data therewith from the un-harmonized medical data based on the medical imaging standard.

10. The data harmonization server of claim 9, wherein the computer readable code, when executed, configures the processor to receive the metadata from the one or more medical servers, the metadata indicating whether the non-functioning template is associated with the un-harmonized medical data.

11. The data harmonization server of claim 10, wherein the computer readable code, when executed, configures the processor to identify the non-functioning template from among a plurality of templates stored in the memory based on one or more of information within a header of the un-harmonized medical data and the metadata.

12. The data harmonization server of claim 9, wherein the computer readable code, when executed, configures the processor to,
recreate an error produced by the one or more medical servers using the non-functioning template, and
determine whether the new template is compatible with a plurality of medical applications using an associated virtual machine.

13. The data harmonization server of claim 9, wherein
the data harmonization server is a repository of templates, and
the processor is configured to push the new template to all of the one or more medical servers.

14. The data harmonization server of claim 13, wherein the processor is configured to periodically push the new template to all of the one or more medical servers.

15. The data harmonization server of claim 9, wherein the new template is a Data Variability Template (DVT) containing the transformation rules for transforming the un-harmonized medical data based on the medical imaging standard.

16. The data harmonization server of claim 9, wherein the un-harmonized medical data received by the data harmonization server is anonymized by removing user information therefrom such that the data harmonization server cannot deduce user information therefrom.

17. A data harmonization system comprising:
a data harmonization server; and
one or more client devices configured to communicate with the data harmonization server, the one or more client devices having a processor configured to,
receive, a template from the data harmonization server, the template including transformation rules for transforming medical data based on a medical imaging standard, the medical data including at least one of patient medical histories, imaging data and test results, and the transformation rules indicating relationships between tags contained in the medical data to transform the medical data from a first format to a second format, each of the first format and the second format being associated with a same modality, transform, using the transformation rules in the template, medical data having the first format to transformed medical data having the second format, determine whether the transformed medical data is harmonized medical data or un-harmonized medical data by comparing the transformed medical data with the medical imaging standard such that the processor of the one or more client devices determines that the transformed medical data is the un-harmonized medical data in response to the transformed medical data being noncompliant with the medical imaging standard, and send the transformed medical data to the data harmonization server, in response to the processor determining that the medical data is un-harmonized medical data.

18. The data harmonization system of claim 17, wherein the template is a Data Variability Template (DVT) containing transformation rules for transforming the medical data based on the medical imaging standard.

\* \* \* \* \*